United States Patent [19]
Gottlieb et al.

[11] Patent Number: 5,985,331
[45] Date of Patent: Nov. 16, 1999

[54] METHODS OF USE OF PHTHALOCYANINES TO INACTIVATE BLOOD BORNE PARASITES

[75] Inventors: Paul Gottlieb, Riverdale; Ehud Ben-Hur; Sara Lustigman, both of New York, all of N.Y.

[73] Assignee: New York Blood Center, Inc., New York, N.Y.

[21] Appl. No.: 08/952,593

[22] PCT Filed: May 14, 1996

[86] PCT No.: PCT/US96/06787

§ 371 Date: Jun. 5, 1998

§ 102(e) Date: Jun. 5, 1998

[87] PCT Pub. No.: WO96/36704

PCT Pub. Date: Nov. 21, 1996

Related U.S. Application Data

[63] Continuation-in-part of application No. 08/444,648, May 19, 1995, abandoned.

[51] Int. Cl.⁶ .......................... A61K 35/14; A61K 35/18; C12N 13/00
[52] U.S. Cl. .......................... 424/529; 424/90; 424/533; 435/173
[58] Field of Search .......................... 424/90, 529, 533; 435/173

[56] References Cited

U.S. PATENT DOCUMENTS

| | | | |
|---|---|---|---|
| 5,120,649 | 6/1992 | Honowitz et al. | 435/173 |
| 5,232,844 | 8/1993 | Honowitz et al. | 435/173.1 |

OTHER PUBLICATIONS

Lancet, Buhl et al, 1295–98 Dec. 2, 1989.

R. Buhl et al., "Systemic Glutathione Deficiency in Symptom-free HIV-Seropositive Individuals", The Lancet, Dec. 2, 1989, pp. 1294–1297.

M. Roederer et al., "N–Acetylcysteine Inhibits Latent HIV Expression in Chronically Infected Cells", AID Research and Human Retroviruses, 1991, 7(6):563–567.

Ben Her et al. 123 CA. 200776y 1995.

*Primary Examiner*—Russell Travers
*Attorney, Agent, or Firm*—Amster, Rothstein & Ebenstein

[57] ABSTRACT

This invention relates to a method for inactivating parasites in blood cell-containing compositions by incubating a mixture of the blood cell-containing composition, a phthalocyanine dye and a quencher and optionally irradiating this mixture with red light. This invention further relates to a method of sterilizing blood cell-containing compositions which contain lipid enveloped viruses and blood borne parasites.

10 Claims, 3 Drawing Sheets

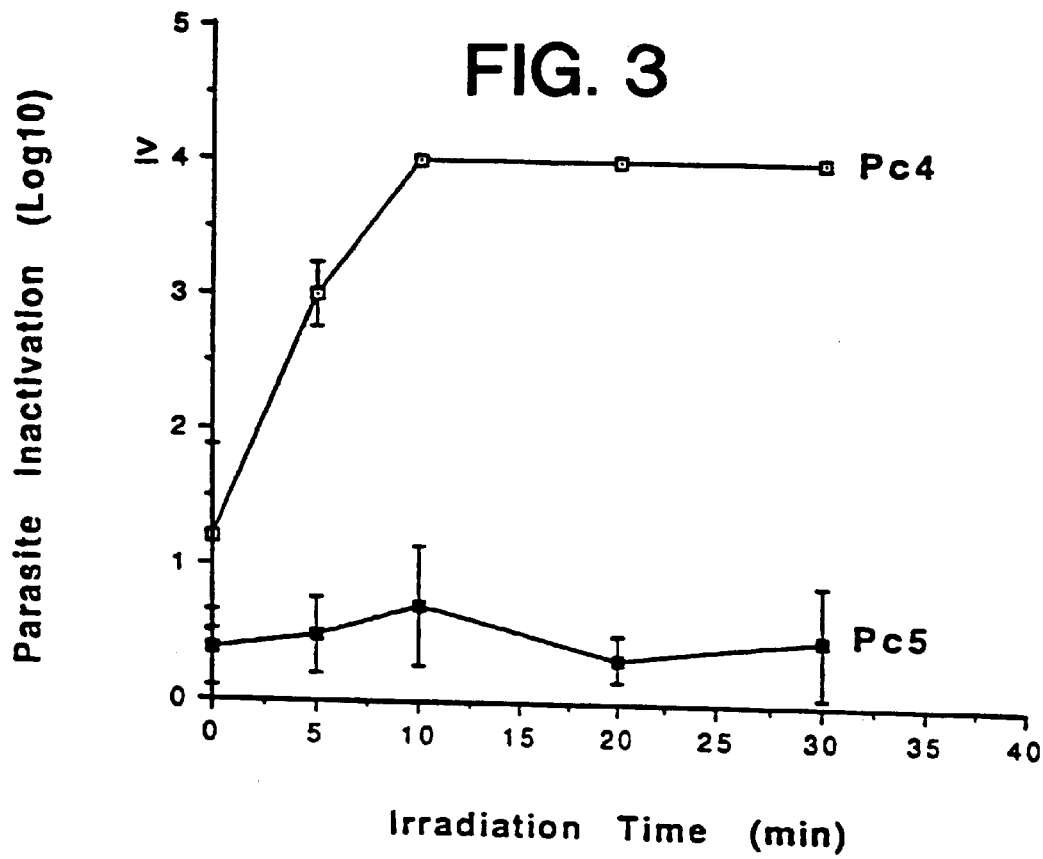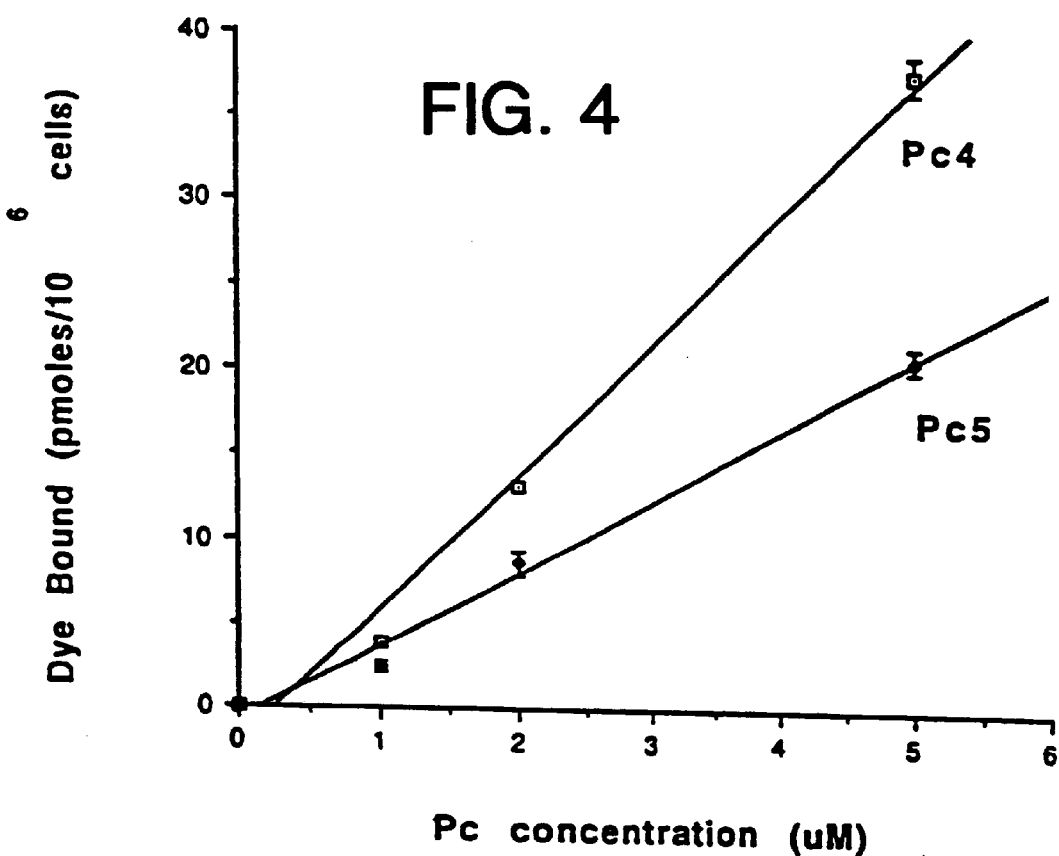

METHODS OF USE OF PHTHALOCYANINES TO INACTIVATE BLOOD BORNE PARASITES

This is a continuation-in-part application of U.S. patent application No. 08/444,648, filed May 19, 1995, now abandoned, the content of which is hereby incorporated by reference in its entirety.

BACKGROUND OF THE INVENTION

1. Field of the Invention

This invention relates to a method for in activating parasites in blood and blood products by incubating a mixture of the blood or blood product, a phthalocyanine dye and a quencher and optionally irradiating this mixture with red light. An advantage of the inventive method is that the treatment, when red light is applied, leads to the inactivation of lipid enveloped virus, also contained in the blood or blood product. A further advantage of the instant method is that while the parasites and lipid enveloped viruses are inactivated, blood cells and labile blood proteins contained in the blood or blood product, are not adversely affected.

2. Description of Related Art

It is estimated that 16 to 18 million people are infected world-wide with Chagas disease. This disease is caused by the parasite *Trypanosoma cruzi* and is endemic to Latin America. A large proportion of immigrants from Latin America to the United States are from areas where the prevalence of the pathogenic agent *T. cruzi* is high. It is estimated that at least 50,000 people infected with *T. cruzi* have emigrated to the U.S.A. In addition to insect vectors, another route of infection is transfusion and this is an emerging problem in the United States. Often the infection caused by *T. cruzi* is chronic and the majority of carriers initially display only mild symptoms. The infectious form of the parasite, trypomastigotes, circulate in the infected individual's blood and is capable of surviving the blood banking process and storage. No serological test for *T. cruzi* in blood banks has been approved by the FDA for use in the U.S.A. at this time. The inadequacy of identification and screening muethods makes it imperative to inactivate the parasite in transfused blood.

While the most serious form of malaria, caused by *Plasmodium falciparum*, is usually transmitted by a mosquito vector, it may also be transmitted by blood transfusion from asymptomatic donors. Almost all blood components, including red cells, platelet concentrates, white cells, cryoprecipitates and fresh plasma transmit malaria. Malaria parasites can survive storage in red blood cells at 2 degrees to 6 degrees for days to weeks or even years. The FDA's Blood Products Advisory Committee has issued recommendations for deferring blood donors at increased risk for malaria, however, these recommendations apply only to donations containing intact red blood cells. Donations used for preparing plasma, plasma components, or derivatives devoid of intact red blood cells are excluded from these regulations. Consequently, absolute safety from transfusion derived malaria is not insured. It is expected that increased immigration and travel from malaria endemic areas will intensify the risk of malaria through transfusion of red blood cell concentrates (RBCC) and platelet concentrates (PC).

Transmission of pathogenic viruses by blood transfusion has been reduced in recent years by serological screening for hepatitis B virus (HBV), hepatitis C virus (HCV) and human immunodeficiency virus (HIV). However, absolute safety has not been achieved and the risk of HBV, HCV and HIV-1 transmission in the USA with a single blood unit has been estimated at 0.0005%, 0.03% and 0.0005%, respectively (R. Y. Dodd, "The Risk of transfusion-transmitted infection", *N. Enc. J. Med.*, 327, 419–21, 1992). Patients who received a large number of RBCC are at a much higher risk of virus transmission. Other viruses of concern in patients with compromised immune systems are cytomegalovirus (CMV) and parvovirus.

Sterilization appears to be the best way to ensure a very high level of safety in transfusion of blood and its components. Currently, all blood products are available in sterilized forms with the exception of red blood cell and platelet concentrates. Sterilization of cellular blood components presents a unique challenge because cell structure and function are disrupted more easily than those of individual proteins. Various approaches have been taken for virus sterilization of red blood cells (RBC) and platelets (B. Horowitz and J. Valinsky, "Inactivation of viruses found with cellular blood components", *Biotechnology of Blood*. J. Goldstein (ed.), pp. 431–52, Buttworth-Heinemann, Stoneham, 1991). However, favorable results were obtained only with photodynamic treatment (PDT) (J. L. Matthews et al., "Photodynamic therapy of viral contaminants with the potential for blood banking applications", *Transfusion* 28, 81–83, 1988). As a result, almost all the efforts are now focused on this approach.

One approach which has been used to sterilize blood and its components is to use psoralens which target nucleic acids and are activated by UVA light. Unfortunately, this approach cannot be used to sterilize RBC. UVA is not effective because of the strong absorption by hemoglobin.

A second approach involves the use of phthalocyanines, which are activated by light in the red light region (650–700 nm). This approach is essentially as set forth in U.S. Pat. Nos. 5,120,649 and 5,232,844 and copending application Ser. Nos. 08/031,787, 08/364,031 and 08/344,919, the entire disclosures of which patents and applications are hereby incorporated by reference. Activation of phthalocyanines by red light in the presence of oxygen is known to result in the disruption of viral membranes. However, nothing is known about the ability of these compounds to inactivate blood borne parasites, particularly protozoa.

Currently, genetian violet (GV) is the only effective agent which may be used for the chemoprophylaxis of *T. cruzi* in endemic areas. This phenylmethane dye is composed of 96% hexamethylparasaniline (crystal violet). It is used at a final concentration of 0.6 mM. The dye is reduced in the organism, forming a carbon centered free radical, which is able to remove oxygen from other molecules or to be added across unsaturated bonds. The carbon-centered free radical can also autooxidize, producing a superoxide anion radical ($O_2$). The latter is converted into $H_2O_2$ by superoxide dismutase. *T. cruzi* is sensitive to $H_2O_2$ since the parasite is deficient in catalase and reduced glutathione (GSH), which degrade peroxide. The interaction between $O_2$ and $H_2O_2$ generates OH, a highly toxic radical. The presence of light enhances this reaction several fold and reducing agents such as ascorbate increase $H_2O_2$ generation. A combination of light exposure and ascorbate will kill parasites using a lesser amount of genetian violet (0.4 mM). The absorption maximum for GV is above 400 nm (R.D. et al., "Light-enhanced free radical formation and trypanocidal action of gentian violet (crystal violet)", *Science*, 229, 1292–95, 1983). GV has proven to be effective in the inactivation of all parasite stages (amastigotes, trypomastigotes and epimastigotes). RBC survival using $^{51}Cr$ as well as blood biochemistry upon storage with GV did not show deleterious effects.

However, there are several side effects associated with GV. First, GV is known to cause microagglutination of the red blood cells. Microagglutination is the clumping of the red blood cells. *In vitro,* this effect is caused by immunoglobulins (IgG) binding to the red blood cell and the effect is observed when viewing a sample of blood under a microscope. A second side effect which is observed when GV is used as chemotherapeutic agent is rouleaux. Rouleaux describes a condition wherein the red blood cells are aligned on top of each other analogous to a stack of coins. It is observed when the blood is collected and allowed to stand in a tube or in a thick portion of blood.

Finally, there are also morphological changes in platelet mitochondria and hemostatic impairment. In recipients, GV turns the blood into a purple color which may stain the skin and mucosa. Furthermore, there is a carcinogenic effect in rodents. Controlled studies to better understand possible toxic effects of this drug are not currently available.

Additionally, antifungal agents with trypanocidal activity have been used to inactivate *T. cruzi* in blood. These include amphotericin B, imidazole derivatives, β-lapachone and 2-nitrodesmethyl imipramine. No human studies have been reported so far for any of these drugs.

There are currently no methods known in the art to inactivate *P. falciparum* in RBCC. Merocyanine 540 has been reported to reduce the concentration of parasitized RBC by 3 $\log_{10}$ when exposed to light (D. M. Smith et al., "Evaluation of merocyanine 540-sensitized photoirradiation as a method for purging malarially infected red cells from blood", *J. Infect Dis.,* 163 1312–17, 1991). However, because there is significant overlap between the absorption spectrum of merocyanine 540 and that of hemoglobin, this dye is not suitable for use in RBCC.

Phthalocyanines (Pc) are porphyrin-like synthetic pigments with a macrocycle made up of four isoindole units linked by nitrogen atoms.

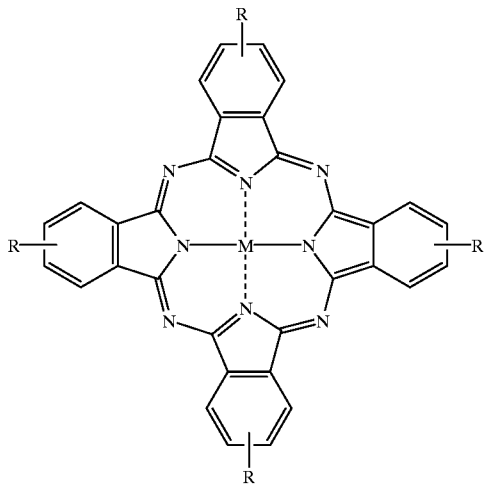

For metals at an oxidation state higher than 2 there are axial ligands which can vary. R can be any substituent, usually sulfonic acid residues.

Phthalocyanines are analogues of porphyrins, with aza nitrogens replacing the methylene bridges and with benzene rings fused onto the pyrrole units. Pc can be derivatized in three ways: substitutions on the benzene rings; changing the central metal ligand; and axial ligands bound to the metal when its valency exceeds 2. Pc are particularly suited for work in RBCC because their high extinction coefficient ($>10^5$/mole-cm) at about 680 nm is far removed from that of hemoglobin. When substituted with diamagnetic metals, Pc have long lived exited triplet state and can generate singlet oxygen at a high quantum yield (*I. Rosenthal et al.,* "The role of molecular oxygen in the photodynamic effect of phthalocyanines", *Radiat. Res.* 107, 136–42, 1968). For a recent review of the photochemistry of phthalocyanines see the article by E. Ben-Hur, "Basic photobiology and mechanisms of action of phthalocyanines", *Photodynamic Therapy: Basic Principles and Clinical Applications,* B. W. Henderson and T. J. Dougherty (eds.), 63–67, Marcel Dekker, N.Y., 1992).

In view of the foregoing, it should be clear that there remains a definite need in the art for a method capable of inactivating blood borne parasites without damaging blood cells or labile blood proteins or causing other effects that would be deleterious for the donor or recipient patient.

SUMMARY OF THE INVENTION

Accordingly, it is an object of the instant invention to inactivate parasites which may be contained in blood or blood products.

Particularly, it is an object of this invention to inactivate parasites in whole blood, red blood cell concentrates and platelet concentrates.

It is a further object of this invention to improve the safety of both whole blood, red blood cell concentrates, platelet concentrates and any products derived therefrom in blood banks.

It is still a further object of this invention to reduce the chance of parasitical infection in animals or men.

It is still a further object of this invention to accomplish all of the foregoing objects while at the same time reducing the chance of viral infection in animals or man.

It is still a further object of this invention to accomplish all of the foregoing objects without adversely affecting cells and labile proteins contained in the blood or blood product.

The above objectives, as well as other objectives, aims and advantages are satisfied by the instant invention.

The present invention relates to a method for inactivating blood borne parasites in blood and blood products. This method entails contacting the blood or blood product suspected of containing the parasite with a phthalocyanine dye and a quencher and optionally irradiating this mixture with red light. A further aspect of this invention is to sterilize blood and blood products which contain the blood borne parasites or blood product. This effect is achieved by irradiating a mixture of the blood, a phthalocyanine dye and a quencher with red light.

BRIEF DESCRIPTION OF THE DRAWINGS

FIG. 3 depicts the rate of trypomastigote inactivation in red blood cell concentrates (RBCC) as a function of irradiation time for Pc4 and Pc5.

FIG. 4 depicts the amount of Pc4 and Pc5 bound to the trypomastigotes in FFP as a function of dye concentration.

FIG. 5*a* depicts untreated cells in which the mitochondrial structure is prominent.

In FIG. 5b and 5c cell damage is observed after treatment with light.

FIG. 5d shows the damage caused by Pc4 to the cells when the reaction is performed in the dark.

DETAILED DESCRIPTION OF THE INVENTION

Figure 1:
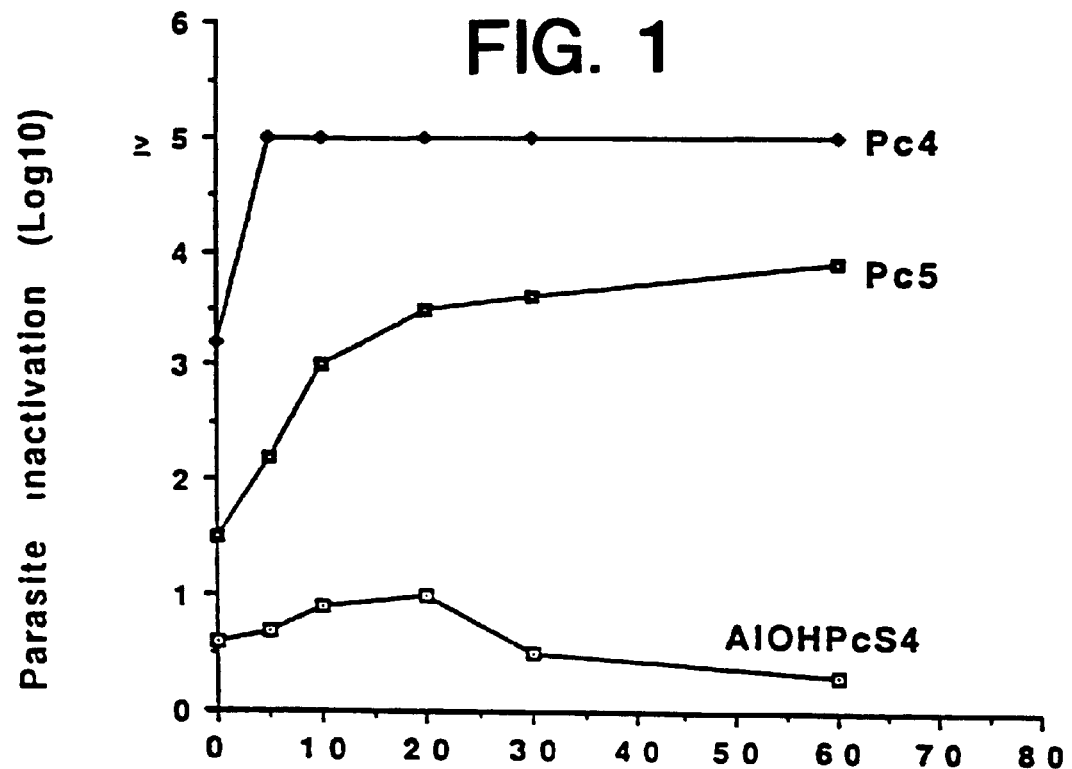
FIG. 1 depicts the rate of *T. cruzi* inactivation in fresh frozen plasma (FFP) as a function of irradiation time for three phthalocyanines, Pc4, Pc5, and $AlOHPcS_4$.

Blood is made up of solids (cells, i.e., erythrocytes, leukocytes, and platelets) and liquid (plasma). The cells are transfused in the treatment of anemia, clotting disorders, infections, etc. In addition, the cells contain potentially valuable substances such as hemoglobin and they can be induced to make other potentially valuable substances such as interferon, growth factors and other biological response modifiers. The plasma is composed mainly of water, salts, lipids and proteins. The proteins are divided-into groups called fibrinogens, serum globulins and serum albumins. Typical antibodies (immune globulins) found in human blood plasma include those directed against infectious hepatitis, influenza H etc.

Blood transfusions are used to treat anemia resulting from disease or hemorrhage, shock resulting from loss of plasma proteins or loss of circulating volume, diseases where an adequate level of plasma is not maintained, e.g., hemophilia and to bestow passive immunization.

With certain diseases one or several of the components of blood may be lacking. Thus the administration of the proper fraction will suffice and the other components will not be wasted on the patient; the other fractions can be used for another patient. The separation of blood into components and their subsequent fractions allows the cells and/or proteins to be concentrated, thus enhancing their therapeutic use.

Cell types found in human blood include red blood cells, platelets and several types of leukocytes. Methods for the preparation of cell concentrates useful in transfusions can be found in *Kirk Othmer's Encyclopedia of Chemical Technology*, Third Edition, Interscience Publishers, Volume 4, pp 25–37, the entire contents of which are hereby incorporated by reference.

Proteins found in the blood cell fraction include hemoglobin, fibronectin, fibrinogen, platelet derived growth factor, superoxide dismutase, enzymes of carbohydrate and protein metabolism etc. In addition, the synthesis of other proteins can be induced, such as interferons and growth factors.

A comprehensive list of inducible leukocyte proteins can be found in Stanley Cohn, et al., "Biology of the Lymphokines", Academic Press, N.Y., 1979.

This invention is directed to a method of inactivating blood borne parasites in blood and blood products. The method entails adding a mixture of phthalocyanine dye and quenchers to the blood or blood product and allowing the resulting mixture to incubate for 30 to 90 minutes. Most preferably a time period of 30 minutes may be used.

The phrase "blood or blood product" is to be construed broadly to include any of the blood and blood products mentioned previously. The phrase includes both blood cell-containing compositions as well as non-cell blood protein-containing compositions. Preferably, the blood is whole blood and the blood product is selected from the group consisting of plasma, a red cell concentrate, a platelet concentrate, and a coagulation factor concentrate.

The method is not required to include an irradiation step. In other words, the method can be conducted in the dark. Accordingly, while one embodiment of the invention contemplates extracorporeal treatment of the blood or blood product, another embodiment of the invention contemplates treatment in vivo.

Thus, the former embodiment broadly relates to a method of inactivating a parasite which may be present in extracorporeal blood or blood product comprising contacting said blood or blood product with a parasiticidally effective amount of a phthalocyanine compound and a quencher. Preferably, the parasite is a protozoa parasite, more preferably, a Plasmodium, e.g., *P. falciparum*, or a Trypanosome, e.g., *T. cruzi*.

This method may also include an irradiation step. In this variation, the incubate obtained in the step above is irradiated with red light at an energy fluence of 5 to 500 J/cm$^2$ for up to 60 minutes. A more preferable range for this fluence is 100 to 500 J/cm$^2$ for 5 to 30 minutes. A most preferable range is irradiating the incubate for 10 minutes, at an energy fluence of 7.5 J/m$^2$. The wavelength of this light is greater than 600 nm, preferably between 650 to 700 nm.

In the inventive methods various phthalocyanine dyes, many of which are already known in the art may be used. Non-limiting examples of phthalocyanines for use in the present invention include:
zinc tetrasulfophthalocyanine, tetrasulfophthalocyanine, aluminum tetranitrophthalocyanine, zinc tetranitrophthalocyanine, tetracarboxyphthalocyanine, GaCl—tetrasulfophthalocyanine, AlCl—tetrasulfophthalocyanine, Gap—tetrasulfophthalocyanine; GaCl—,AlCl— or Ga-tetranitrophthalocyanine.

A preferred embodiment of this invention involves the use of cationic phthalocyanine Pc5 (HOSiPcOSi $(CH_3)_2(CH_2)_3N^+(CH_3)_3I^-$) and its neutral analogue Pc4 (HoSiPcoSi $(CH_3)_2(CH,)_3N(CH_3)_2$). The dyes are added to the blood or blood product to a concentration of the dye of up to 12 $\mu$M. Preferable concentrations for the dyes are 1 to 5 $\mu$M, most preferably 2 $\mu$M.

Any quenchers which will scavenge free radicals or reactive oxygen species, e.g., singlet oxygen, may be used alone or in combination. Types of quenchers contemplated include mannitol, glutathione (GSH), vitamin E, and Trolox. These quenchers may be present in an amount of 4 to 5 mM. A most preferable combination is 5 mM of Trolox and 4 mM of GSH.

In the above mixtures, diluents may be used as carriers. Typical diluents include cremophor (soybean oil emulsion), DMSO, Tween 50 or water. Additionally, Trager's buffer or $NH_4Cl$ may be employed. Trager's buffer contains 0.57 M NaCl, 0.58 M KCl, 10.0 mM $NaH_2PO_4$, 70.0 mM $K_2HPO_4$, 0.11 M $NaHCO_3$, and glucose.

A further aspect of this invention is-a method of sterilizing blood or blood products from lipid enveloped viruses and blood borne-parasites. This method entails adding a mixture of the phthalocyanine dye and a quencher to the blood or blood product, incubating the mixture and irradiating the mixture with red light. Examples of viruses that can be inactivated in this manner are HBV, NANBHV (e.g., HCV) and HIV-1. However, for a more detailed list of such viruses, please see the aforementioned patents and applications. Examples of blood borne parasites include those discussed above.

The conditions described in the aforementioned patents and applications for inactivating viruses are also generally applicable here for the inactivation of blood borne parasites. Those conditions are shown in those patents and applications to be protective of blood cells and labile blood proteins. Accordingly, the instant method is likewise protective of blood cells and labile blood proteins. In general, red cells and platelets retain at least 70% and, preferably, greater than 80% and, more preferably, greater than 95% of structural integrity. Structural integrity of red cells is measured by counting the number of red cells remaining after said treatment or by assaying the amount of hemoglobin released from said red cells as a result of said treatment. For example, if at least 70% of said red cells remain after said treatment or if less than 30% of the initial hemoglobin is released after said treatment, then a structural integrity of at least 70% of said red cells has been retained. Similarly, structural integrity of platelets is determined by counting the number of platelets remaining after said treatment or by determining the aggregation of the platelets as compared to an untreated control upon the addition of a biological aggregation agent, for example, collagen. In the case of labile blood proteins, a recovery of at least 70% and, preferably, greater than 80% and, more preferably, greater than 95% is achieved. Methods for assaying labile blood protein activity and other methods for assaying structural and functional integrity of blood cells are disclosed in the aforementioned patents and applications.

Phthalocyanines have an intense absorption in the far red which is ideal for PDT of cancer and sterilization of red cells, as there is little absorption by hemoglobin at these wavelengths. However, the relative contributions of type I and type II photodynamic reactions in biological systems is not known and appears to vary from system to system. Nevertheless, preferred are use of quencher mixtures calculated to quench both type I and type II reactions or of individual quencher compounds capable of quenching both type I and type II reactions.

As noted previously, also contemplated is a therapeutic treatment of patients infected with blood borne parasites. This aspect of the invention broadly relates to a method of treating a patient infected with a blood borne parasite comprising administering to said patient a parasiticidally effective amount of a phthalocyanine compound.

Administration of the phthalocyanine can be by any conventional route but preferably is intravenous. For administration the phthalocyanine and the quencher are admixed in a pharmaceutically acceptable excipient, particularly, cremophor, DMSO or ethanol. Preferred quenchers are selected from the group consisting of vitamin E, Trolox, reduced glutathione mannitol and mixtures thereof. A particularly preferred mixture of phthalocyanine and quencher is Pc4 in 5 mM of Trolox and 4 mM of GSH with cremophor as the diluent. Then, this mixture is administered to the patient in one or more daily dosages so that the patient receives a daily effective dose such that the final concentration in the blood is from $2\mu M$ to $5\mu M$ and such treatment is continued for a 1 to 2 month duration.

The invention will now be described in the following non-limiting examples.

EXAMPLES

EXAMPLE 1

*T. cruzi* inactivation

This example tests Pc dye-quencher mixtures and light for parasite sterilization of RBCC, specifically the application of the neutral Pc derivative, Pc4. The dye is used at a concentration of $2 \mu M$ and is added to a solution containing 5 mM of Trolox and 4 mM of GSH. The mixture is then allowed to incubate 30 minutes in the dark followed by radiation with red light (>600nm) for at least 10 minutes at an energy fluence of 25 mW/cm². Under these conditions >$4\log_{10}$ TCID$_{50}$ of *T. cruzi* trypomastigote forms were inactivated. For irradiation, tissue culture adapted *T. cruzi* strain Y, propagated on LLC-MN (monkey kidney) cells, are added at $1\times10^6$/ml into RBCC along with the dye and quenchers. Serial dilutions in growth media of the treated parasite cell suspensions are added into the wells of 96 microliter plates, preplated with $1\times10^5$ LLC-MK2 cells. The plates are scored for the presence of trypomastigotes after 10 to 14 days incubation of 37 degrees in a $CO_2$ incubator.

EXAMPLE 2

*T. cruzi* inactivation for the dark reaction

This example tests the toxicity of PC-quencher mixtures to parasites in the dark. Pc4 is used at a concentration of 2 $\mu M$ and is added to a solution containing 5 mM Trolox and 4 mM of GSH. The mixture is then allowed to incubate in the dark. Under these conditions about 3 $\log_{10}$ of the trypomastigotes were killed.

EXAMPLE 3

*T. cruzi* survival

Tissue culture adapted *T. cruzi* strain Y, propagated on LLC-MK2 cells were added at $1\times10^6$/ml into RBCC diluted 1:1 in PBS. Following Pc-red light treatment serial dilution in growth medium of cell suspension were prepared. The RBC were hemolyzed prior to these dilutions by diluting the cell suspension ten times into 0.85% $NH_4Cl$, pH 7.2, the parasites were centrifuged and resuspended in growth medium. The diluted parasite suspension (0.1 ml) was added into wells of 96 microliter plates plated with $1\times10^5$ LLC-MK2 cells. The plates were scored under microscope for the presence of trypomastigotes after 5 days of incubation at 37° C. in a $CO_2$ incubator and after 12 days. The titer of *T. cruzi* was calculated by the Spearman-Karber method (S. C. Callender et al., "Microcomputer applications and technology," *Laboratory Medicine*, 21, 241–50 (1993) (Table I)).

EXAMPLE 4

*P. falciparum* survival

Highly synchronized ring-stage parasites of *P. falciparum* 7G8, a Brazilian isolate, were used for the inactivation assays. Uninfected RBCC at equivalent density were added to achieve 1% starting parasitemia. The parasitized RBC were diluted in 3 ml Trager's buffer to yield hematocrit of 35%. The Pc derivatives and quenchers were added to a final 2 $\mu M$ concentration. Cell suspensions were kept in the dark for 30 min before irradiation with red light at 25 mW/cm² for up to 20 min. Cell suspensions exposed to chemicals in the dark, to solvent and light for 20 min or to neither chemical nor light nor solvent served as controls. Photosensitized, control cells and aliquots containing pretreatment parasitemia were seeded into 24 well culture dish and diluted with fresh culture medium to make 5% final hematocrit and 1% parasitemia. Cultures were monitored by microscopic examination of Giemsa-stained thin smears. Cultures were incubated for 48 h at 37° C. to permit the maturation of schizonts, release of merozoites and formation of new ring stage parasites (Table 1).

TABLE 1

Inactivation of *T. cruzi* and *P. falciparum* by Pc + red light in RBCC

| TREATMENT (RBCC were irradiated with 25 mW/cm² in the prescence of Pc, 5 mM Trolox and 4 mM GSH) | | Log kill of *T. cruzi* trypmastigotes 12 days after treatment | % parasitemia of *P. falciparum* 48 h after treatment |
|---|---|---|---|
| Pc (2 μM) | Light (min) | | |
| NONE | 0 | 0 | 12 |
| Pc5 | 0 | 0 | 5 |
| Pc5 | 5 | 0 | 3.5 |
| Pc5 | 10 | 0 | 0.5 |
| Pc5 | 20 | 0 | <0.025 |
| Pc4 | 0 | 1.9 | 1 |
| Pc4 | 5 | >3.2 | <0.025 |
| Pc4 | 10 | >3.2 | <0.025 |

As shown in Table 1, Pc4 is effective in killing both parasites. The most interesting and surprising result is that there is a reduction of the development of the parasite in the dark. Pc4 without exposure to light have caused 1.9 log kill of *T. cruzi* and the inhibition of development of *P. falciparum* by 92%. The 1% parasitemia that was observed after exposure to Pc4 without red light is probably the result of persistence of the original parasites as the stage of the parasites was trophozoites which were very sick and could not probably develop further from the trophozoite state parasites to ring stage parasites.

In. the following examples, *T. cruzi* trypomastigote inactivation was performed as follows. Samples of RBCC or fresh frozen plasma (FFP) were spiked from the stock trypomastigote preparation to obtain about $10^6$ parasites/ml. The reaction mixtures included Trolox (Aldrich Chemical Corp.) at 5 mM and glutathione (GSH, Sigma) at 4 mM. During irradiation, 400 μl aliquots were removed at the various times and diluted 10 times into growth medium. These were centrifuged for 9 minutes at 2700×g and the pellet resuspended into 600 μl DMEM. The resuspended samples were then 10 fold serially diluted and 50 μl of each dilution was inoculated into 40% confluent LCC-MK$_2$ cells grown in 96 well microtiter plates and incubated at 37° C. for 10 to 14 days. After the incubation time period, each well was scored for the presence or absence of trypomastigote forms.

EXAMPLE 5

Parasite Inactivation in FFP

This example tests the rate of *T. cruzi* trypomastigote inactivation in FFP for three phthalocyanines Pc4, Pc5 and AlOHPcS$_4$. Each dye was tested at a concentration of 2 μM in the presence of a standard quencher mixture. FIG. 1 shows the treatment of the parasites with the neutral dye Pc4 resulted in complete inactivation of the trypomastigotes ($\geq 5.0$ log$_{10}$) after 5 min of irradiation with red light at 25 mW/cm² (7.5 J/cm²). Using the cationic dye Pc5, about 3.9 log$_{10}$ kill was observed after 60 min of light exposure (90 J/cm²). The anionic dye AlOHPcS$_4$ displayed a maximum of about 1.0 log$_{10}$ inactivation (FIG. 1). Pc4 caused a substantial inactivation even in the absence of light, about 3.2 log$_{10}$ kill (FIG. 1).

Figure 2:
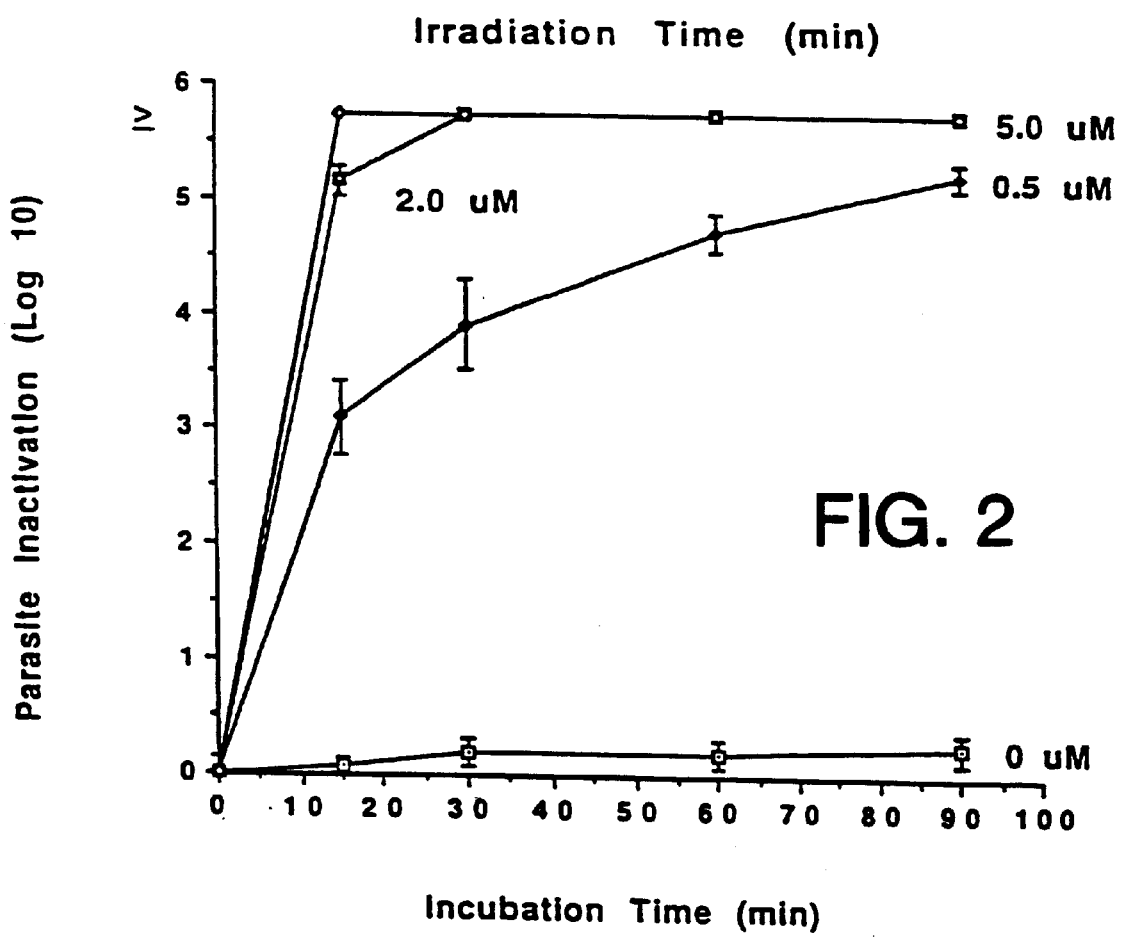
FIG. 2 depicts the rate of trypomastigote inactivation as a function of concentration for Pc4 for reactions.

The Pc4 concentration dependence of inactivation is shown in FIG. 2 for dark conditions. Complete ($\geq 5.5$ log$_{10}$) inactivation was observed at 2 μM and above; however, at 0.5 μM Pc4 4.5 log$_{10}$ inactivation was noted. In the dark, complete inactivation ($\geq 5.5$ log$_{10}$) was achieved at 5 μM Pc4 (at the symbol $\geq$) and at 2 FM Pc4.

EXAMPLE 6

Parasite Inactivation in RBCC

This example tests the rate of trypomastigote inactivation by Pc4 and Pc5 in RBCC as a function of irradiation time as shown (see FIG. 3). The rate of inactivation was slower than that observed in FFP. Thus, at 5 min of light exposure, there was 3 log$_{10}$ reduction of trypomastigote infectivity. In the absence of light, there was 1.2 log$_{10}$ infectivity loss. It took 10 min of light exposure for complete kill ($\geq 4.0$ log$_{10}$).

EXAMPLE 7

Pc4 and Pc5 Binding to Trypomastigotes

This example tests the extent of binding of Pc4 and Pc5 to the trypomastigote in FFP (see FIG. 4). Trypomastigotes at $10^6$ were suspended in FFP with Pc4 or Pc5, Trolox and GSH for 30 min at 25° C. The parasite cells were then pelleted by centrifugation and washed six times with PBS at $10^6$ ml and the emission spectra at 650–700 nm ($\lambda_{ex}=607$ nm) was recorded using a Shimadzu model RF1501 spectrofluorometer. Quantitation of dye bound to the cells was made using standard curve.

From 2 μM to 5 μM, Pc4 was found to bind about twice as much as Pc5 to the parasites. At a dye concentration of 2 μM, there were 13 pmoles Pc4 bound per $10^6$ parasites, while there were 8.6 pmoles Pc5 bound under the same conditions. Binding was linearly dependent on concentration for both dyes.

EXAMPLE 8

Ultrastructural Analysis

This example tests the extent of the damage of the cells to elucidate the mechanism of parasite inactivation by photodynamic treatment using electron microscopy.

Trypomastigotes were suspended in PBS or FFP with the dye and quenchers as described above. After irradiation of the reaction mix, aliquots of the samples were added to an equal volume of a fixative containing 8% paraformaldehyde, 4% glutaraldehyde in 0.2 M phosphate buffer. The cell suspension was pelleted by centrifugation, and sections produced by microtome were stained with uranyl acetate. Transmission electron microscopy was performed upon a Philips model 410 electron microscope.

Figure 5:
FIG. 5 shows the effect of photodynamic treatment on the structural integrity of the cells.

Untreated cells display a prominent mitochondrion structure with a deeply staining, elongated kinetoplast visible (FIG. 5a). The most evident alteration observed after treatment was in this structure. When treatment was in PBS or FFP, mitochondrial swelling was observed with a shearing effect upon the kinetoplast structure (FIGS. 5b and 5c). Some cell damage was detected within the sample treated with Pc4 in the absence of light (FIG. 5d). The damage does not appear as extensive and involves some vacuolization. This limited damage might account for the observed dark toxicity of Pc4 in the infectivity experiments.

EXAMPLE 9

Light and Dark Inactivation of *P. falciparum*

Erythrocytes infected with ring-stage *P. falciparum* parasites (5 to 10% parasitemia, >90% ring-stage), were diluted with fresh A+ RBC to yield 1% parasitemia and 35% hematocrit in Trager's buffer (W. Trager, *Exp. Parasitol.*, 8:265–73 (1959)) or 60% hematocrit in pooled A+ human serum culture medium. Samples of 3 ml were aliquoted in polystyrene tubes (Fisher Scientific Inc., Springfield, N.J.) and were treated with a final concentration of 2 $\mu$M Pc 4 or Pc 5 in the presence of 5 mM Trolox (Aldrich Chemical Corp., Milwaukee, Wis.), 4 mM mannitol (Sigma Chemical Co., St. Louis, Mo.) and 4 mM glutathione (Sigma Chemical Co., St. Louis, Mo.). Cell suspensions were kept in the dark for 30 min at room temperature before irradiation for up to 40 min. The cells were irradiated with red light at 25° C. using a xenon short arc lamp (Oriel Corp., Stratford, Conn.) equipped with a cutoff filter (Vincent Lighting Systems, Cleveland, Ohio) transmitting at wavelengths >600 nm. Irradiance at the sample surface, measured with a photometer (Model IL 1350, International Light, Newburyport, Mass.) was 25 mW/cm$^2$. During irradiation the samples were rotated and rolled on a hematology mixer (Fisher Scientific, Inc.) to obtain an even exposure. As a result, a thin film of RBCC was formed on the tube walls, which facilitated light transmittance through the suspension. Cell suspensions exposed to chemicals in the dark, to solvent and light for 40 min, or to neither chemical nor light nor solvent served as controls. Aliquots of photosensitized and control cells were spun and resuspended in fresh culture medium (RPMI-1640, 25 mM HEPES, 28.6 mM NaHCO3, 360 $\mu$M hypoxanthine, 10 $\mu$g/ml gentamicin) to 5% final hematocrit, and then 1 ml of diluted cells were seeded in quadruplicates into 24 well culture plates. The growth medium was replaced the next day, and the parasitemia levels were determined after 48 hours by staining thin smears with Giemsa reagent and microscopic examination of 1000–4000 cells. The sensitivity of detection is thus 1 in 4000 (0.025%).

In a first experiment, erythrocytes parasitized by 7G8 clone of *P. falciparum* (1% parasitemia; >90% ring stage), a Brazilian isolate, were treated as described above at 35% hematocrit. The degree of parasitemia was determined following 48 hr culture after treatment. The results are shown in Table 2 below. Both Pc 4 and Pc 5 were effective to reduce parasitemia below the detection limit, but Pc 4 worked very fast, reducing parasitemia below the detection limit after only 5 min light exposure. For comparison, inactivation of $\geq$5 log VSV and *T. cruzi* with Pc 4 requires 20 min and 10 min light exposure, respectively, under the same conditions.

TABLE 2

Inactivation of *P. falciparum* by phthalocyanines

| Phthalocyanine (2 $\mu$M) | Light (min) | Parasitemia (%) | Inactivation (%) |
|---|---|---|---|
| None | 0 | 12.5 | 0 |
| None | 30 | 12.5 | 0 |
| Pc4 | 0 | 1 | 92 |
| Pc4 | 5 | <0.025 | $\geq$99.8 |
| Pc4 | 10 | <0.025 | $\geq$99.8 |
| Pc5 | 0 | 5 | 60 |
| Pc5 | 5 | 3.5 | 72 |
| Pc5 | 10 | 0.5 | 96 |
| Pc5 | 20 | <0.025 | $\geq$99.8 |

In a second experiment, erythrocytes parasitized by HB3 clone of *P. falciparum*, a chloroquine sensitive isolate, were treated exactly as described above for the first experiment, except that the hematocrit during treatment was 60%. The results are shown in Table 3 below. As shown in Table 3, there was a light dose dependent reduction of parasitemia under these conditions, but, as compared to 35% hematocrit, complete parasite kill using 60% hematocrit required a longer period of time.

TABLE 3

Inactivation of *P. falciparum* by Pc 4

| Pc 4 ($\mu$M) | Light (min) | Parasitemia (%) | Inactivation (%) |
|---|---|---|---|
| 0 | 0 | 4.5 | 0 |
| 0 | 30 | 4.5 | 0 |
| 2 | 0 | 1.6 | 65 |
| 2 | 5 | 1.2 | 73 |
| 2 | 10 | 0.8 | 82 |
| 2 | 20 | 0.4 | 91 |
| 2 | 40 | <0.025 | $\geq$99.5 |

Table 2 also shows that PC 4 in the absence of light caused the inhibition of the development of *P. falciparum* by 92% at 35% hematocrit. The 1% parasitemia observed in these cultures after exposure of cells to Pc 4 was due to the original parasites that were seeded. The parasites, which were at the stage of trophozoites, were developmentally degenerated, crisis form, and could therefore not develop further from the trophozoite stage to ring stage parasites. When this experiment was repeated with the HB3 isolate and 35% or 65% hematocrit, the dark effect was reproduced with 99% and 65% inhibition of development, respectively.

It will be appreciated that the instant specification and claims are set forth by way of illustration and not limitation, and that various modifications and changes may be made without departing from the spirit and scope of the present invention.

What is claimed is:

1. A method of treating a patient infected with a blood borne protozoa parasite comprising administering to said patient a parasiticidally effective amount of a phthalocyanine compound to treat said patient.

2. The method according to claim 1, wherein the phthalocyanine is selected from the group consisting of Pc4 or Pc5.

3. The method according to claim 1, wherein the phthalocyanine is administered to the patient along with a quencher.

4. The method according to claim 3, wherein the quencher is selected from the group consisting of vitamin E, Trolox, reduced glutathione, mannitol and mixtures thereof.

5. The method according to claim 1, wherein said parasite is selected from the group consisting of *Plasmodium falciparum* and *Trypanosoma cruzi*.

6. The method according to claim 1, further comprising exposing said patient to a parasiticidally effective amount of red light.

7. The method according to claim 6, wherein the phthalocyanine is selected from the group consisting of Pc4 or Pc5.

8. The method according to claim 6, wherein said red light is of a wavelength $\geq$600 nm.

9. The method according to claim 6, wherein the phthalocyanine is administered to the patient along with a quencher.

10. The method according to claim 9, wherein the quencher is selected from the group consisting of vitamin E, Trolox, reduced glutathione, mannitol and mixtures thereof.

* * * * *